United States Patent
Madison

(10) Patent No.: US 9,227,090 B2
(45) Date of Patent: *Jan. 5, 2016

(54) METHOD FOR LIGHTENING SKIN

(75) Inventor: Stephen Alan Madison, Newton, CT (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/908,248

(22) Filed: Oct. 20, 2010

(65) Prior Publication Data

US 2011/0033404 A1   Feb. 10, 2011

Related U.S. Application Data

(62) Division of application No. 12/141,561, filed on Jun. 18, 2008.

(51) Int. Cl.
A61Q 19/02 (2006.01)
A61K 8/36 (2006.01)
A61K 8/44 (2006.01)
A61Q 17/04 (2006.01)

(52) U.S. Cl.
CPC ............ *A61Q 19/02* (2013.01); *A61K 8/361* (2013.01); *A61K 8/44* (2013.01); *A61Q 17/04* (2013.01)

(58) Field of Classification Search
CPC ......... A61Q 19/02; A61Q 17/04; A61K 8/44; A61K 8/361

See application file for complete search history.

(56) References Cited

U.S. PATENT DOCUMENTS

| | | | |
|---|---|---|---|
| 4,096,240 A | 6/1978 | Mathur | |
| 5,262,153 A | 11/1993 | Mishima et al. | |
| 5,399,785 A * | 3/1995 | Miura et al. | 568/766 |
| 5,429,816 A | 7/1995 | Hofrichter et al. | |
| 5,516,511 A | 5/1996 | Motley et al. | |
| 5,591,424 A | 1/1997 | Hofrichter et al. | |
| 5,650,144 A | 7/1997 | Hofrichter et al. | |
| 5,744,130 A | 4/1998 | Guskey et al. | |
| 5,776,494 A | 7/1998 | Guskey et al. | |
| 5,863,546 A | 1/1999 | Swinehart | |
| 5,965,113 A | 10/1999 | Guskey | |
| 5,968,489 A | 10/1999 | Swaile et al. | |
| 5,998,423 A | 12/1999 | Manneth et al. | |
| 6,033,651 A | 3/2000 | Dolak et al. | |
| 6,139,880 A | 10/2000 | Dolak et al. | |
| 6,153,177 A * | 11/2000 | Bartolone et al. | 424/62 |
| 6,171,581 B1 | 1/2001 | Joshi et al. | |
| 6,171,601 B1 | 1/2001 | Gardlik et al. | |
| 6,183,730 B1 | 2/2001 | Guskey et al. | |
| 6,197,343 B1 | 3/2001 | Minami et al. | |
| 6,280,764 B1 | 8/2001 | Fotinos | |
| 6,352,688 B1 | 3/2002 | Scavone et al. | |
| 6,365,137 B1 | 4/2002 | Aust et al. | |
| 6,423,325 B1 * | 7/2002 | Alaluf et al. | 424/401 |
| 6,680,285 B2 | 1/2004 | Abbas et al. | |
| 6,713,051 B2 | 3/2004 | Mayes et al. | |
| 6,835,373 B2 | 12/2004 | Kolodzik et al. | |
| 6,849,251 B2 | 2/2005 | Banowski et al. | |
| 6,875,425 B2 | 4/2005 | Harichian | |
| 6,932,984 B1 | 8/2005 | Babtsov | |
| 6,936,242 B2 | 8/2005 | Elliott et al. | |
| 7,247,294 B1 | 7/2007 | Shore et al. | |
| 7,250,158 B1 | 7/2007 | Shore et al. | |
| 8,247,405 B2 | 8/2012 | Madison | |
| 2002/0106384 A1 | 8/2002 | Zhang | |
| 2002/0192243 A1 | 12/2002 | Hsu et al. | |
| 2003/0039672 A1 | 2/2003 | Ginger et al. | |
| 2004/0043044 A1 | 3/2004 | Granger et al. | |
| 2004/0081672 A1 * | 4/2004 | Gupta | 424/401 |
| 2004/0208902 A1 | 10/2004 | Gupta | |
| 2004/0253275 A1 | 12/2004 | Eini et al. | |
| 2005/0120917 A1 | 6/2005 | Ruger | |
| 2005/0220726 A1 | 10/2005 | Pauly et al. | |
| 2006/0067960 A1 | 3/2006 | Russ et al. | |
| 2006/0115441 A1 | 6/2006 | James et al. | |
| 2007/0253911 A1 | 11/2007 | Tamarkin et al. | |
| 2008/0193393 A1 | 8/2008 | Dayan | |

FOREIGN PATENT DOCUMENTS

| | | |
|---|---|---|
| CA | 2 493 176 | 2/2004 |
| EP | 0 423 929 | 4/1991 |
| FR | 2 735 688 | 12/1996 |
| GB | 2230186 A | 10/1990 |
| JP | 05201847 A | 8/1993 |
| JP | 05306231 | 11/1993 |
| JP | 05345705 | 12/1993 |

(Continued)

OTHER PUBLICATIONS

Wiechers, J.W., A.V. Rawlings, C. Garcia, C. Chesne, P. Balaguer, J.C. Nicolas, S. Corre, and M.D. Galibert. 2005. A new mechanism of action for skin whitening agents: binding to the peroxisome proliferation-activated receptor. Int. J. Cosmet. Sci. Apr; 27(2): Abstract.*
Weindl et al., *Peroxisome Proliferator-Activated Receptors and their Ligands*, Drugs, 2005, 66, pp. 1919-1934.
Kang et al., *Expression and function of peroxisome peroxisome-activated receptors in human melanocytes*, British Journal of Dermatology 2004, 150, pp. 462-468.
PCT International Search Report and Written Opinion on INternaitonal Application No. PCT/EP2009/056886 dated Oct. 28, 2009.
Yamamoto Naomi et al., "*Skin-Lightening Preparations Containing Hydroxycarboxylic Acids and Vitamins*", Caplus Host—Caplus, Sep. 1995, XP002258109, abstract.
Database WPI Week 199437. Thomas Scientific, 1994-299657, XP002550562 & JP 06 227939 A, 1994.
Co-pending application for: Applicant: Madison, U.S. Appl. No. 12/141,561, filed Jun. 18, 2008, entitled: Compositions for Lightening Skin Color.

(Continued)

*Primary Examiner* — Johann R Richter
*Assistant Examiner* — David Browe
(74) *Attorney, Agent, or Firm* — Edward A. Squillante, Jr.

(57) ABSTRACT

Skin lightening additives and skin lightening compositions having at least one of a heterosubstituted, saturated or unsaturated aliphatic acid are described. The compositions are suitable for topical application and may comprise 12-hydroxystearic acid, ricinoleic acid or both.

22 Claims, No Drawings

(56) References Cited

FOREIGN PATENT DOCUMENTS

| JP | 06065042 | 3/1994 |
|---|---|---|
| JP | 07025742 | 1/1995 |
| JP | 07033634 | 2/1995 |
| JP | 08092055 | 4/1996 |
| JP | 08092056 | 4/1996 |
| JP | 09012442 | 1/1997 |
| JP | 09052817 | 2/1997 |
| JP | 09087135 | 3/1997 |
| JP | 09157129 | 6/1997 |
| JP | 10203921 | 8/1998 |
| JP | 10265321 | 10/1998 |
| JP | 10265322 | 10/1998 |
| JP | 11029430 | 2/1999 |
| JP | 11124308 | 5/1999 |
| JP | 11246343 | 9/1999 |
| JP | 2000143479 | 5/2000 |
| JP | 2000302661 | 10/2000 |
| JP | 2001163755 | 6/2001 |
| JP | 2001181173 | 7/2001 |
| JP | 2001206833 | 7/2001 |
| JP | 2002265387 | 9/2002 |
| JP | 2002284664 | 10/2002 |
| JP | 2003055697 | 2/2003 |
| JP | 2003306419 | 10/2003 |
| JP | 2004075645 | 3/2004 |
| JP | 2004115381 | 4/2004 |
| JP | 2004238394 | 8/2004 |
| JP | 2004262853 | 9/2004 |
| JP | 2005002050 | 1/2005 |
| JP | 2005503379 | 2/2005 |
| JP | 2002179516 | 6/2006 |
| JP | 2006219423 | 8/2006 |
| JP | 3919123 | 5/2007 |
| JP | 2008150314 | 7/2008 |
| WO | WO0170189 A1 | 9/2001 |
| WO | 03/013462 | 2/2003 |
| WO | WO2004017935 A1 | 3/2004 |
| WO | WO2006010214 A1 | 2/2006 |
| WO | 2006/056283 | 6/2006 |
| WO | 2006/103091 | 10/2006 |
| WO | WO2006117055 A1 | 11/2006 |
| WO | WO2007039058 A2 | 4/2007 |
| WO | WO2008015490 A1 | 2/2008 |
| WO | WO2008086403 A1 | 7/2008 |
| WO | WO2008105632 A1 | 9/2008 |

OTHER PUBLICATIONS

Blending nature & Science-Innovative natural products, The Herbarie Nov. 2007, Nov. 1-2, 2007, ., DE.
Kamillenol blau, Omikron Naturhaus Prdukt Information, Dec. 1-3, 1995, ., DE.
Matricaria oil, Natural Fairness skin lightening, Jan. 2005, ., ., US.
Scn-care-Recommendations on use of CO2, CO2 extracts Scin-care, Sep. 1-3, 2004, ., US.
Loizzo et al., Natural products and their Derivatives as Cholinesterase INhibitors in the Treatment of Neurodegenerative Disorders: An Update, Current Medicinal Chemistry, Jan. 1, 2008, 1209-1223, 15.
Scarpa et al, Depigmenting procedures and drugs employed by Melanoderm Populations, Journal of Ethnopharmacology, 1987, 17-66, 19, Elsevier Scientific Publications Ltd, IT.
Walcezek, Herstellung and Charakerisjerung eines, Dissertation, 2002, 1-142, ., DE.
Lee et al., "PPAR-gamma agonist, ciglitazone, increases pigmentation and migration of human melanocytes", Experimental Dermatology vol. 16, pp. 118-123, 2007.
Wineski et al., Phenoxyethanol as a nontoxic preservative in the dissection laboratory, Acta Anat Basel, 1989, 155-8 (Abstract), 136(2).

\* cited by examiner

METHOD FOR LIGHTENING SKIN

This application is a continuation of U.S. Ser. No. 12/141,561, entitled Compositions for Lightening Skin Color, filed Jun. 18, 2008.

FIELD OF THE INVENTION

The present invention is directed to a skin lightening additive as well as compositions comprising the same. More particularly, the present invention is directed to a cosmetic composition comprising a skin lightening additive whereby the skin lightening additive comprises a heterosubstituted, saturated or unsaturated aliphatic acid, or a mixture thereof. The skin lightening additive, when used, results in a cosmetic composition that can provide moisturizing benefits. Moreover, it has been unexpectedly discovered that such aliphatic acids have skin lightening benefits when topically applied.

BACKGROUND OF THE INVENTION

Many consumers are concerned with the characteristics of their skin. For example, consumers are concerned with the degree of pigmentation of their skin, freckles and/or age spots. Other consumers wish to reduce skin darkening caused by exposure to sunlight. To meet the needs of consumers, many attempts have been made to develop products that improve skin characteristics. The products developed thus far, however, often tend to have low efficacy, undesirable side effects or both. Furthermore, such products can be expensive and are often not an alternative for lower income consumers.

There is an increasing interest to develop a cosmetic composition that comprises new skin lightening additives. This invention, therefore, is directed to cosmetic compositions that comprise new skin lightening additives. The cosmetic compositions of the present invention preferably comprise, as a lightening additive, compounds like 12-hydroxystearic acid, ricinoleic acid or both. The cosmetic compositions of this invention result in a decrease in melanin content which is at least about 8% lower (preferably, at least about 11% lower) when comparing MelanoDerm™ cultures treated with the same to MelanoDerm cultures that have not been subjected to a composition with the newly discovered skin lightening additives of this invention.

ADDITIONAL INFORMATION

Efforts have been disclosed for making skin care cosmetic compositions. In U.S. Pat. No. 6,875,425, skin lightening agents with 4-substituted resorcinol derivative compounds are described.

Other efforts have been disclosed for making skin treatment compositions. In U.S. Pat. Nos. 7,250,158 and 7,247,294, methods for treating with skin lightening agents are described.

Still other efforts have been disclosed for treating skin. In U.S. Pat. No. 5,998,423, compositions with polycyclic nitrogen heterocycles are described.

None of the additional information above describes skin lightening compositions that comprise, as a lightening additive, a heterosubstituted, saturated or unsaturated aliphatic acid, or mixture thereof.

SUMMARY OF THE INVENTION

In a first aspect, the present invention is directed to a skin lightening additive, the skin lightening additive comprising a heterosubstituted, saturated or unsaturated aliphatic acid, or both.

In a second aspect, the present invention is directed to a cosmetic composition for skin lightening, the cosmetic composition comprising a skin lightening agent comprising the skin lightening additive of the first aspect of this invention.

In a third aspect, the present invention is directed to a method for lightening skin with the cosmetic composition of the second aspect of this invention.

All other aspects of the present invention will more readily become apparent upon considering the detailed description and examples which follow.

As used herein, a decrease in melanin content means a melanin content decrease when comparing two (2), three week old MatTek MelanoDerm cultures that have not been treated with a composition comprising the skin lightening additive of this invention to two (2), three week old MatTek MelanoDerm cultures that have been treated with a composition comprising the skin lightening additive of this invention wherein treated means:

(a) placing the MelanoDerm culture within a six (6) well tissue culture dish and set about 0.3 cm off of the tissue culture dish;

(b) subjecting the MelanoDerm culture to 0.1 and 5 micromolar compositions having the skin lightening additive of this invention, the composition being one prepared from a 10 millimolar solution of skin lightening additive and carrier (e.g., dimethyl sulfoxide) having been diluted with Dulbecco's Modified Eagle Media; and (c) comparing the treated and untreated cultures by obtaining average melanin content (expressed in micrograms) by extracting melanin from MelanoDerm and obtaining absorbance readings at 490 nm (OD490) using a commercially available spectrophotometer like a Hach Spectrophotometer.

Cosmetic composition, as used herein, is meant to include a composition for topical application to skin of mammals, especially humans. Such a composition may be generally classified as leave-on or rinse off, and is meant to include conditioners or tonics, lipsticks, color cosmetics, and general topical compositions that in some fashion and at the very least, reduce the effect of melanin on keratinocytes. Lightening and whitening as used herein are meant to mean the same and they include the lightening of skin directly as well as the lightening of spots on the skin, like age spots and freckles. Dulbecco's Modified Eagle Media means the nutrient solution sold by MatTek Corporation and treated and used according to instructions supplied with the product commercially identified as MEL30010BBLLMM. Skin lightening additive means a component suitable to result in physical, but especially biological whitening (i.e., a reduction in melanin production) whereby the skin lightening additive can comprise, consist essentially of or consist of the skin lightening additive. MelanoDerm means the product having normal, human-derived epidermal keratinocytes and melanocytes which have been cultured to form a multilayered, highly differentiated model of the human epidermis, all of which is made commercially available by MatTek Corporation. Unsaturated, as used herein, means having at least one bond that is not $sp^3$ hybridized. Comprising, as used herein, is meant to include consisting essentially of and consisting of:

The cosmetic composition of the present invention can be in the form of a liquid, lotion, cream, serum, gel, soap bar or toner, or applied via a face mask or patch. The composition of this invention is one that at the very least, lightens skin when skin is meant to include skin on the face, neck, chest, back, arms, hands, legs and scalp. All ranges identified herein are meant to implicitly include all ranges subsumed therein, if, for example, reference to the same is not explicitly made.

DETAILED DESCRIPTION OF THE PREFERRED EMBODIMENTS

The only limitation with respect to the skin lightening additive that may be used in this invention is that the same may be used in a topical composition suitable for use on humans. The preferred additive is a heterosubstituted, saturated or unsaturated aliphatic acid or a mixture thereof.

In a most preferred embodiment, the skin lightening additive employed in the present invention comprises a compound having the formulae:

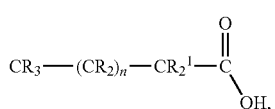

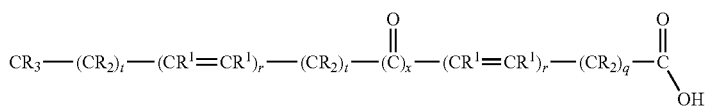

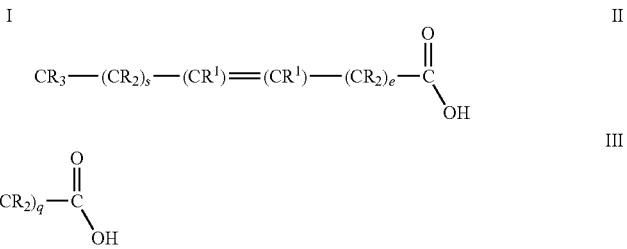

or a mixture thereof,
wherein each R is independently hydrogen, hydroxyl, $C_{1-6}$ alkoxy, $C_{1-6}$ alkyl, arylalkyl or an amine, with the proviso that at least one R group comprises a heteroatom; each $R^1$ is independently hydrogen, $C_{1-6}$ alkoxy, $C_{1-6}$ alkyl, arylalkyl or an amine; n is an integer from about 7 to about 19; and s and e are each independently an integer from about 0 to about 8, where $s+e \geq 6$; q is an integer from about 6 to about 11; each r is independently an integer from 0 to 1, with the proviso that each r is not 1 when x is 1; x is an integer from 0 to 1 with the proviso that x is 0 when at least one r is 1; and each t is independently an integer from 1 to 7.

The preferred compounds suitable for use in this invention (either alone or in a mixture) are aleuritic acid; phloionolic acid; 9,10,13-trihydroxy-1'-octadecenoic acid; 9,13-dihydroxy-12-ethoxy-10-octadecenoic acid; 9-hydroxy-10,12-octadecadienoic acid; 4,14-dihydroxy-octadecanoic acid; 12-hydroxystearic acid (12-hydroxyoctadecanoic acid); lesquerolic acid; ricinelaidic acid; ambrettolic acid, and rincinoleic acid (12-hydroxy-9-cis-octadecanoic acid) as represented by either formula I or II. Other preferred compounds suitable for use in this invention include beta-dimorphecolic acid; densipolic acid; 8-methoxy-13-hydroxy-9,11-octadecadienoic acid; 7-oxo-octadecanoic acid; 9-oxo-octadecanoic acid; 12-oxo-octadecanoic acid and 10-oxo-14-methyl-pentadecanoic acid as represented by formula III. Furthermore it is within the scope of the present invention to include any derivative (like an ester derivative) and/or salt of the acid represented by formulae I-III, and especially, Mg, Na and/or Ca salts thereof. Such compounds are commercially available from suppliers like Vertellus Specialties, Inc., Welch, Home & Clark Co., Inc., as well as Croda Chemicals.

The cosmetic compositions of the present invention typically comprise from about 0.001 to about 15% by weight, and preferably, from about 0.1 to about 12%, and most preferably, from about 1 to about 10% by weight skin lightening additive, based on total weight of the cosmetic composition and including all ranges subsumed therein.

While it is within the scope of this invention for the skin lightening additive to consist essentially of and to consist of heterosubstituted, saturated or unsaturated aliphatic acid or a mixture thereof, in an often desired embodiment, the skin lightening additive of this invention comprises from about 0.2 to about 95%, and preferably, from about 10 to about 85%, and most preferably, from about 30 to about 65% by weight heterosubstituted saturated or unsaturated aliphatic acid, or a mixture thereof, based on total weight of skin lightening additive and including all ranges subsumed therein.

In yet another desired embodiment, the cosmetic composition of this invention comprises from about 2 to about 9%, and preferably, from about 3 to 8%, and most preferably, from about 3 to about 6% by weight heterosubstituted, saturated or unsaturated aliphatic acid, or a mixture thereof, based on total weight of the cosmetic composition and including all ranges subsumed therein.

When used in combination, the weight ratio of heterosubstituted, saturated or unsaturated aliphatic acid to heterosubstituted, saturated aliphatic acid is from about 5:95 to about 95:5, and preferably, from about 20:80 to about 80:20, and most preferably, from about 40:60 to about 60:40, including all ratios subsumed therein.

It should be known that commercially acceptable and conventional vehicles may be used, acting as diluents, dispersants and/or carriers for the skin lightening agents and additives described herein and for any other optional but often preferred additives. Therefore, the cosmetically acceptable vehicle suitable for use in this invention may be aqueous-based, anhydrous or an emulsion whereby a water-in-oil or oil-in-water emulsion is generally preferred. If the use of water is desired, water typically makes up the balance of the cosmetic composition, and preferably, makes up from about 5 to about 99%, and most preferably, from about 40 to about 80% by weight of the cosmetic composition, including all ranges subsumed therein.

In addition to water, organic solvents may be optionally included to act as carriers or to assist carriers within the compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils like isopropyl myristate, cetyl myristate, 2-octyldodecyl myristate, avocado oil, almond oil, olive oil, neopentylglycol dicaprate, mixtures thereof or the like. Typically, such ester oils assist in emulsifying the cosmetic composition of this invention, and an effective amount is often used to yield a stable, and most preferably, water-in-oil emulsion.

Emollients may also be used, if desired, as carriers within the cosmetic composition of the present invention. Alcohols like 1-hexadecanol (i.e., cetyl alcohol) and phenoxyethanol are often desired as are the emollients generally classified as silicone oils and synthetic esters. Silicone oils suitable for use include cyclic or linear polydimethylsiloxanes containing from 3 to 9, preferably from 4 to 5, silicon atoms. Nonvolatile silicone oils useful as an emollient material in the inventive cosmetic composition described herein include polyalkyl siloxanes, polyalkylaryl siloxanes and polyether siloxane copolymers. The essentially non-volatile polyalkyl siloxanes useful herein include, for example, polydimethylsiloxanes.

The ester emollients that may optionally be used are:
(1) Alkenyl or alkyl esters of fatty acids having 10 to 20 carbon atoms. Examples thereof include isoarachidyl neopentanoate, isononyl isonanonoate, oleyl myristate, coleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, stearyl stearate and arachidyl behenate.
(5) Sterols esters, of which cholesterol fatty acid esters are examples.

Emollients when used, typically make up from about 0.1 to about 50% by weight of the cosmetic composition, including all ranges subsumed therein.

Fatty acids having from 10 to 30 carbon atoms may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used as an optional carrier.

Humectants of the polyhydric alcohol type may also be employed in the cosmetic compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.2 to 25%, and preferably, from about 0.5 to about 15% by weight of the cosmetic composition, based on total weight of the cosmetic composition and including all ranges subsumed therein.

Thickeners may also be utilized as part of the cosmetically acceptable carrier in the cosmetic compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

Surfactants may also be present in cosmetic compositions of the present invention. Total concentration of the surfactant will range from about 0 to about 40%, and preferably, from about 0 to about 20%, optimally from about 0 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isothionates, acyl glutamates, $C_8$-$C_{20}$ alkyl ether phosphates and combinations thereof.

Perfumes may be used in the cosmetic composition of this invention. Illustrative non-limiting examples of the types of perfumes that may be used include those comprising terpenes and terpene derivatives like those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid, citronellic acid, or cis-geranic acid nitrile, mixtures thereof or the like.

Preferably, the amount of fragrance employed in the cosmetic composition of this invention is in the range from about 0.0% to about 10%, more preferably, about 0.00001% to about 5 wt %, most preferably, about 0.0001% to about 2%.

Various types of optional additional active ingredients may be used in the cosmetic compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, peroxides, zinc salts, and sunscreens.

Beta-hydroxy acids include salicylic acid, for example. Zinc pyrithione is an example of the zinc salts useful in the cosmetic composition of the present invention.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-e, respectively. The exact amount of sunscreen employed in the compositions can vary depending upon the degree of protection desired from the sun's UV radiation.

Additives that reflect or scatter the suns rays may also be employed. These additives include oxides like zinc oxide and titanium dioxide.

Many cosmetic compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1%/0 to 2% by weight of the composition.

Still other optional ingredients that may be used with the cosmetic composition of this invention include dioic acids (e.g., malonic acid, sebacic acid), antioxidants like vitamin E, vitamins, like niacinamide and vitamin C and its derivatives, resorcinols and its derivatives (including those esterified with, for example, ferulic acid, vanillic acid or the like) and retinoids, including retinoic acid, retinal, retinol and retinyl esters, conjugated linoleic acid, petroselinic acid and mixtures thereof, as well as any other conventional ingredients well known for wrinkle-reducing, skin whitening, anti-acne effects and reducing the impact of sebum.

The cosmetic compositions of the present invention are intended for use primarily as a product for topical application to human skin, especially and at least as a product for lightening the skin. Thus, the inventor has discovered that the described aliphatic acids have excellent skin lightening capabilities whereby the same may be employed as skin lightening additives in topical cosmetic compositions that are applied topically to areas of the skin where lightening or whitening is desired. Other benefits may include skin moisturizing, decreasing the effect of sebum on the skin and skin wrinkle reducing. Often, the cosmetic composition of the present invention has a melting point from about 30° C. to about 45° C., including all ranges subsumed therein. In an especially preferred embodiment, the cosmetic composition of the present invention has a pH from about 4.5 to about 7.5, including all ranges subsumed therein.

When making the cosmetic composition of the present invention, the desired ingredients are mixed in no particular order and usually at temperatures from about 70 to about 80° C. and under atmospheric pressure.

The packaging for the composition of this invention can be a patch, bottle, tube, roll-ball applicator, propellant driven aerosol device, squeeze container or lidded jar.

The examples which follow are provided to illustrate and facilitate an understanding of the invention. The examples are not intended to limit the scope of the claims.

Examples

Commercially available human skin equivalents (MelanoDerem™ from MatTek) were obtained for testing the impact of heterosubstituted, saturated or unsaturated aliphatic acid on melanogenesis. Solutions having a final concentration of 0.1 to 5 micromolar were prepared from a 10 millimolar dimethyl sulfoxide stock solution and dosed ten (10) times in a three (3) week period into the media of the MelanoDerm cultures. The media consisted of commercially available basal Dulbecco's Modified Eagles media, prepared and treated in the manner set forth in the manufacturer's instructions. For long term maintenance of the MelanoDerms, the basal media was supplemented with bFGF and alpha MSH to stimulate melanocyte growth and melanogenesis. Each treatment condition was done in duplicate and three (3) sets were made for each treatment, as well as for a control (culture not treated with the aliphatic acid). The cultures were maintained at a temperature of about 37° C. and incubated in a humidified, 5% $CO_2$ incubator during the dosing period, but removed while being dosed.

After a three (3) week period, the MelanoDerm cultures were removed and solubilized in a centrifuge tube containing 250 microliters of Solvable reagent (GNE9100, Packard) for sixteen (16) hours (overnight) in a 60° C. oven. Following solubilization, the centrifuge tube containing the sample was spun at 12,000 g for five (5) minutes. Two hundred (200) microliters of supernatant were removed and placed in a ninety-six (96) well plate. A spectrophotometer was used to measure the absorbance of the supernatant at 490 nm. A standard curve using synthetic melanin was set up in parallel to allow quantitation of melanin, in micrograms, of the samples. The results are provided below:

TABLES

| Active | | Average MC | ΔMC |
|---|---|---|---|
| | MC* Value Range | | |
| Control | 76.0-78.4 | 77.2 | — |
| Aliphatic acid[i] | 67.9-69.2 | 68.6 | 8.6 |
| | MC Value Range | | |
| Control | 76.0-78.4 | 77.2 | — |
| Aliphatic acid[ii] | 69.9-67.6 | 68.8 | 8.4 |

[i] = ricinoleic acid (0.1 uM)
[ii] = 12-hydroxystearic acid (5 uM)
*MC = melanin content The results, as they relate to MelanoDerm cultures, show that cosmetic compositions with the aliphatic acids of this invention unexpectedly result in skin lightening.

What is claimed is:

1. A method for lightening skin comprising the steps of:
   a) identifying skin where skin lightening is desired;
   b) contacting the skin with a composition comprising from about 0.001 to about 15% by weight of 12-hydroxystearic acid and/or a salt and/or an ester thereof as the only skin lightening active and a cosmetic carrier; and
   c) lightening skin
   wherein the composition is capable of lightening skin with 12-hydroxystearic acid as the only skin lightening additive in the composition, the composition optionally comprising an additional component selected from the group consisting of dioic acid, stearic acid, sunscreen and a mixture thereof.

2. The method according to claim 1 wherein the dioic acid is present and comprises malonic acid or sebacic acid.

3. The method according to claim 1, wherein the composition further comprises a beta-hydroxy acid, sunscreen, or a mixture thereof.

4. The method according to claim 1, wherein the composition comprises about 2 to about 9 percent by weight 12-hydroxystearic acid and/or a salt and/or an ester thereof as the single skin lightening additive.

5. The method according to claim 1 wherein the composition does comprise sunscreen.

6. The method according to claim 4 wherein the composition does comprise sunscreen.

7. The method according to claim 1 wherein the composition further comprises phenoxyethanol as preservative.

8. The method according to claim 1 wherein the composition further comprises silicone, humectants and thickener.

9. The method according to claim 1 wherein the single skin lightening additive in the composition is 12-hydroxystearic acid which makes up from about 0.001 to about 12% by weight of the composition.

10. The method according to claim 1 wherein 12-hydroxystearic acid and/or a salt and/or an ester thereof makes up from about 0.1 to about 10% by weight of the composition.

11. The method according to claim 1 wherein the composition is in the form of a leave-on lotion, cream, serum, gel or toner, or is applied with a patch or face mask.

12. The method according to claim 1 wherein the composition is applied directly to spots on skin to lighten the spots where skin lightening is desired.

13. The method according to claim 3 wherein the composition is applied directly to spots on skin to lighten the spots where skin lightening is desired.

14. The method according to claim 1 wherein the composition is applied directly to skin to reduce melanin production.

15. The method according to claim 14 wherein the composition further comprises sunscreen, preservative, titanium oxide, zinc oxide, a cellulosic derivative, a mixture thereof.

16. The method according to claim 1 wherein the skin is skin on the face or hands, and the composition does comprise thickener, octyl methoxycinnamate or both.

17. The method according to claim 1 wherein the skin is skin on the face or hands.

18. The method according to claim 1, wherein the composition is applied directly to skin to reduce melanin production and the composition does comprise methyl paraben, propyl paraben or a mixture thereof.

19. The method according to claim 1 wherein the composition is a leave-on lotion, cream or serum.

20. The method according to claim 1 wherein the composition is in the form of a leave-on lotion.

21. The method according to claim 3 wherein the composition is a leave-on lotion, cream or serum.

22. The method according to claim 1 wherein the composition does comprise sunscreen and has a pH from about 4.5 to about 7.5.

\* \* \* \* \*